United States Patent
Shinoda et al.

(10) Patent No.: US 9,798,921 B2
(45) Date of Patent: Oct. 24, 2017

(54) WRINKLE CARE SUPPORT DEVICE AND METHOD FOR SUPPORTING WRINKLE CARE

(71) Applicant: Panasonic Intellectual Property Management Co., Ltd., Osaka (JP)

(72) Inventors: Masayo Shinoda, Tokyo (JP); Rieko Asai, Osaka (JP); Chie Nishi, Kanagawa (JP); Tetsuro Sato, Kanagawa (JP); Kaori Ajiki, Osaka (JP); Tomofumi Yamanashi, Kanagawa (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 68 days.

(21) Appl. No.: 14/919,714

(22) Filed: Oct. 21, 2015

(65) Prior Publication Data
US 2016/0154992 A1 Jun. 2, 2016

(30) Foreign Application Priority Data
Nov. 28, 2014 (JP) .................................. 2014-241748

(51) Int. Cl.
G06K 9/00 (2006.01)
G06T 11/60 (2006.01)
A61B 5/00 (2006.01)

(52) U.S. Cl.
CPC .......... *G06K 9/00228* (2013.01); *A61B 5/442* (2013.01); *A61B 5/7275* (2013.01);
(Continued)

(58) Field of Classification Search
CPC ........... G06K 9/00228; G06K 9/00234; G06K 9/00248; G06K 9/00261; G06K 9/00268;
(Continued)

(56) References Cited

U.S. PATENT DOCUMENTS 8,391,639 B2* 3/2013 Hillebrand ............. G06T 11/60
345/639
8,597,284 B2* 12/2013 Castro .................... A61N 5/062
606/9
(Continued)

FOREIGN PATENT DOCUMENTS

JP 3-118036 5/1991
JP 2009-518125 5/2009
(Continued)

OTHER PUBLICATIONS

The Extended European Search Report dated Mar. 30, 2016 for the related European Patent Application No. 15191831.5.
(Continued)

*Primary Examiner* — Jose Couso
(74) *Attorney, Agent, or Firm* — Greenblum & Bernstein, P.L.C.

(57) ABSTRACT

A wrinkle care support device includes: a wrinkle change detector that detects a change made in a wrinkle after occurrence of the wrinkle, the wrinkle having occurred in skin by provision of predetermined stimulation; a wrinkle care information determiner that determines, based on the detected change, user presentation information relating to wrinkle care; and an information outputter that outputs the determined user presentation information. Note that the wrinkle care support device may further include: an image obtainer that obtains an image where the skin is photographed; and a wrinkle detector that detects the wrinkle from the obtained image. The detection of the change may include a detection of a wrinkle disappearing time starting from when the predetermined stimulation is provided until the wrinkle is no longer detected.

20 Claims, 15 Drawing Sheets

(52) U.S. Cl.
CPC .............. *A61B 5/742* (2013.01); *G06T 11/60* (2013.01); *A61B 5/0077* (2013.01); *A61B 5/7282* (2013.01)

(58) Field of Classification Search
CPC ........... G06K 9/00295; G06K 9/00362; G06K 2009/00322; G06K 2009/00328; G06T 11/60; G06T 2207/30196–2207/30201; A61B 5/442; A61B 5/7275; A61B 8/742; A61B 5/7282; A61B 5/0077; A61B 5/445; A61B 5/0059; A61B 18/203; A61B 2018/0047; A61B 2018/00738; A61B 2017/00747; A61B 2018/00452; A61B 2018/00458; A61H 7/008; A61H 9/005; A61H 9/0057; A61M 5/422; A61F 2013/0028; A61F 2013/00374; A61Q 19/08; A61N 5/0616; A61N 2005/067
See application file for complete search history.

(56) References Cited

U.S. PATENT DOCUMENTS

| | | | |
|---|---|---|---|
| 2007/0125390 A1* | 6/2007 | Afriat | A61B 5/442 128/898 |
| 2010/0185064 A1* | 7/2010 | Bandic | A61B 5/0059 600/306 |
| 2015/0044317 A1* | 2/2015 | Farmer | A61Q 19/08 424/780 |
| 2015/0230863 A1* | 8/2015 | Youngquist | A61B 18/203 606/9 |

FOREIGN PATENT DOCUMENTS

| | | |
|---|---|---|
| JP | 2009-236610 | 10/2009 |
| JP | 2011-056189 | 3/2011 |
| WO | 2007/067536 | 6/2007 |
| WO | 2009/014832 | 1/2009 |

OTHER PUBLICATIONS

Venkataraman K et al: "A kinematic-variational model for animating skin with wrinkles", Computers and Graphics, Elsevier, GB, vol. 29, No. 5, Oct. 1, 2005 (Oct. 1, 2005), pp. 756-770, XP027759658.

Osamu Kuwazuru et al., "Wrinkle Characteristics Analysis of Human Skin with Age-Related Alteration of Mechanical Properties" Journal of the Japan Society for Simulation Technology, 2009, vol. 1, No. 4, pp. 66-73.

Masamitsu Ichihashi et al., "Glycation Stress and Photo-Aging in Skin" Anti-Aging Medicine 8(3): pp. 23-29, 2011.

Satoshi Sato "Changes in Dermal Extensibility and Contractility Associated with Aging" Journal of the Japan Geriatrics Society, Jul. 1982, vol. 19, No. 4, pp. 376-380.

* cited by examiner

FIG. 3

| USER'S AGE | WRINKLE DISAPPEARING TIME | WRINKLE TYPE |
|---|---|---|
| 10S | LESS THAN 1 SECOND | TEMPORARY |
| | 1–2 SECONDS | POTENTIAL |
| | 2 SECONDS OR MORE | EXISTENT |
| 20S | LESS THAN 1 SECOND | TEMPORARY |
| | 1–3 SECONDS | POTENTIAL |
| | 3 SECONDS OR MORE | EXISTENT |
| 30S | LESS THAN 2 SECONDS | TEMPORARY |
| | 2–4 SECONDS | POTENTIAL |
| | 4 SECONDS OR MORE | EXISTENT |
| 40S | LESS THAN 2 SECONDS | TEMPORARY |
| | 2–6 SECONDS | POTENTIAL |
| | 6 SECONDS OR MORE | EXISTENT |
| OVER 50S | LESS THAN 3 SECONDS | TEMPORARY |
| | 3–8 SECONDS | POTENTIAL |
| | 8 SECONDS OR MORE | EXISTENT |

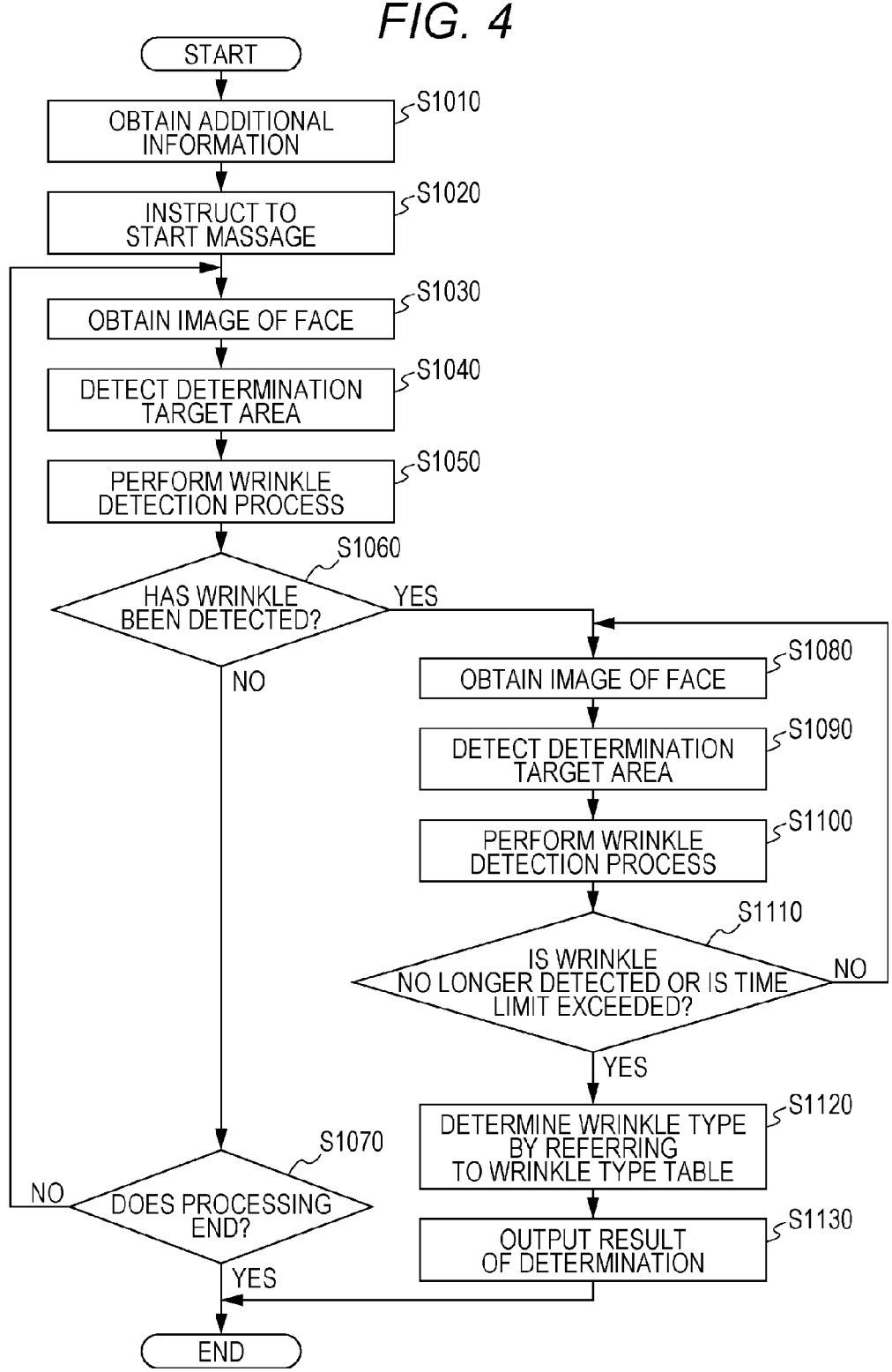

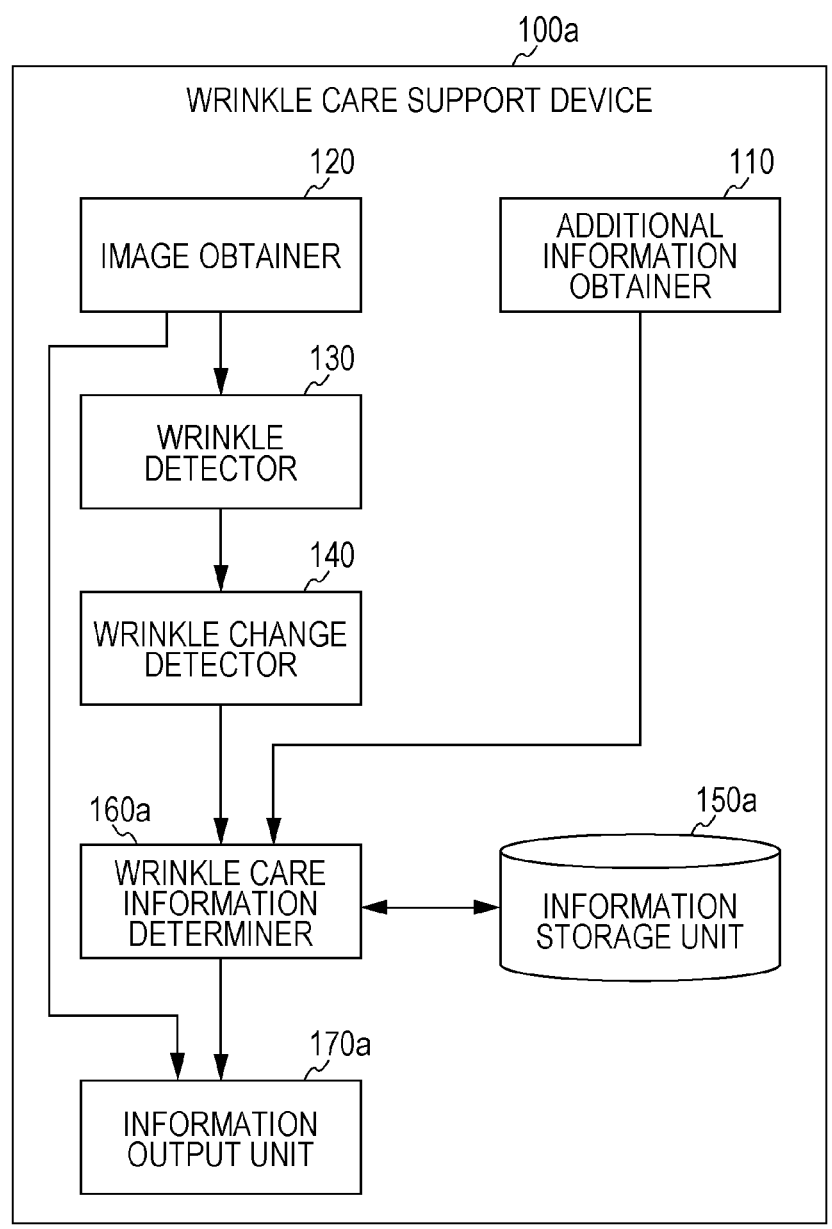

| USER'S AGE (221a) | WRINKLE DISAPPEARING TIME (222a) | SUGGESTED CARE DETAILS (223a) |
|---|---|---|
| 10S | 1 – 2 SECONDS | HOURS OF SLEEP, DIET, AND CLEANSING METHOD |
| 20S | 2 – 2.2 SECONDS | HOURS OF SLEEP, DIET, AND CLEANSING METHOD |
|  | 2.2 – 2.8 SECONDS | ADD MASSAGE AND MOISTURIZERS |
|  | 2.8 – 3 SECONDS | ADD SUPPLEMENTS AND MUSCLE STRENGTHENING |
| 30S | 2 – 2.5 SECONDS | HOURS OF SLEEP, DIET, AND CLEANSING METHOD |
|  | 2.5 – 3.5 SECONDS | ADD MASSAGE, MOISTURIZERS, AND SUPPLEMENTS |
|  | 3.5 – 4 SECONDS | ADD MUSCLE STRENGTHENING AND PROTECTION AGAINST ULTRAVIOLET RADIATION |
| 40S | 2 – 3 SECONDS | DIET AND MASSAGE |
|  | 3 – 5 SECONDS | ADD MOISTURIZERS AND SUPPLEMENTS |
|  | 5 – 6 SECONDS | ADD MUSCLE STRENGTHENING AND PROTECTION AGAINST ULTRAVIOLET RADIATION |
| OVER 50S | 3 – 4 SECONDS | DIET, MASSAGE, MOISTURIZERS |
|  | 4 – 7 SECONDS | ADD SUPPLEMENTS |
|  | 7 – 8 SECONDS | ADD MUSCLE STRENGTHENING AND PROTECTION AGAINST ULTRAVIOLET RADIATION |

| USER'S AGE (231b) | PRE-CARE WRINKLE DISAPPEARING TIME (T0) (232b) | REDUCTION RATE OF POST-CARE WRINKLE ELIMINATING TIME (T): (T−T0)/T0 (233b) | DETERMINATION (234b) |
|---|---|---|---|
| 10S | 1−2 SECONDS | 10% OR MORE | EFFECTIVE |
| | | LESS THAN 10% | NOT EFFECTIVE |
| 20S | 2−2.2 SECONDS | 10% OR MORE | EFFECTIVE |
| | | LESS THAN 10% | NOT EFFECTIVE |
| | 2.2−2.8 SECONDS | 20% OR MORE | EFFECTIVE |
| | | LESS THAN 20% | NOT EFFECTIVE |
| | 2.8−3 SECONDS | 10% OR MORE | EFFECTIVE |
| | | LESS THAN 10% | NOT EFFECTIVE |
| 30S | 2−2.5 SECONDS | 10% OR MORE | EFFECTIVE |
| | | LESS THAN 10% | NOT EFFECTIVE |
| | 2.5−3.5 SECONDS | 20% OR MORE | EFFECTIVE |
| | | LESS THAN 20% | NOT EFFECTIVE |
| | 3.5−4 SECONDS | 10% OR MORE | EFFECTIVE |
| | | LESS THAN 10% | NOT EFFECTIVE |
| 40S | 2−3 SECONDS | 10% OR MORE | EFFECTIVE |
| | | LESS THAN 10% | NOT EFFECTIVE |
| | 3−5 SECONDS | 20% OR MORE | EFFECTIVE |
| | | LESS THAN 20% | NOT EFFECTIVE |
| | 5−6 SECONDS | 10% OR MORE | EFFECTIVE |
| | | LESS THAN 10% | NOT EFFECTIVE |
| OVER 50S | 3−4 SECONDS | 10% OR MORE | EFFECTIVE |
| | | LESS THAN 10% | NOT EFFECTIVE |
| | 4−7 SECONDS | 20% OR MORE | EFFECTIVE |
| | | LESS THAN 20% | NOT EFFECTIVE |
| | 7−8 SECONDS | 10% OR MORE | EFFECTIVE |
| | | LESS THAN 10% | NOT EFFECTIVE |

FIG. 13

| USER'S AGE | PRE-CARE WRINKLE DISAPPEARING TIME (T0) | DETAILS OF NEXT CARE FOR A CASE IN WHICH CARE IS NOT EFFECTIVE |
|---|---|---|
| 10S | 1 – 2 SECONDS | ADD MASSAGE AND MOISTURIZERS |
| 20S | 2 – 2.2 SECONDS | ADD MASSAGE AND MOISTURIZERS |
| | 2.2 – 2.8 SECONDS | ADD SUPPLEMENTS AND MUSCLE STRENGTHENING |
| | 2.8 – 3 SECONDS | RECOMMEND CONSULTATION AT CLINIC |
| 30S | 2 – 2.5 SECONDS | ADD MASSAGE, MOISTURIZERS, AND SUPPLEMENTS |
| | 2.5 – 3.5 SECONDS | ADD MUSCLE STRENGTHENING AND PROTECTION AGAINST ULTRAVIOLET RADIATION |
| | 3.5 – 4 SECONDS | RECOMMEND CONSULTATION AT CLINIC |
| 40S | 2 – 3 SECONDS | ADD MOISTURIZERS AND SUPPLEMENTS |
| | 3 – 5 SECONDS | ADD MUSCLE STRENGTHENING AND PROTECTION AGAINST ULTRAVIOLET RADIATION |
| | 5 – 6 SECONDS | RECOMMEND CONSULTATION AT CLINIC |
| OVER 50S | 3 – 4 SECONDS | ADD SUPPLEMENTS |
| | 4 – 7 SECONDS | ADD MUSCLE STRENGTHENING AND PROTECTION AGAINST ULTRAVIOLET RADIATION |
| | 7 – 8 SECONDS | RECOMMEND CONSULTATION AT CLINIC |

WRINKLE CARE SUPPORT DEVICE AND METHOD FOR SUPPORTING WRINKLE CARE

BACKGROUND

1. Technical Field

The present disclosure relates to a wrinkle care support device and a method for supporting wrinkle care that support measures to reduce skin wrinkles.

2. Description of the Related Art

Conventionally, for the purpose of reducing skin wrinkles, various types of measures such as massage and application of serum are widely taken. In recent years, there has been increasing market demand for measures that include not only a reduction in already existent wrinkles, but also prevention of an increase in wrinkles (hereinafter, the measures are referred to as "wrinkle care" as appropriate).

In view of this, for example, it is considered to use a technique described in PTL 1. The technique described in PTL 1 (hereinafter, referred to as "conventional technique") detects displacement at various parts of skin occurring when a facial expression or orientation is changed. It can be said that a part with larger displacement than parts around the part is where wrinkles are likely to occur. Therefore, by using such a conventional technique, it is possible to detect parts where wrinkles are likely to occur, and to efficiently perform wrinkle care for preventing an increase in wrinkles.

CITATION LIST

Patent Literatures

PTL 1: Japanese Translation of PCT Publication No. 2009-518125
PTL 2: Unexamined Japanese Patent Publication No. H03-118036

Non-Patent Literatures

NPL 1: Osamu Kuwazuru and two others, "Wrinkle Characteristics Analysis of Human Skin with Age-Related Alteration of Mechanical Properties", Journal of the Japan Society for Simulation Technology, 2009, Vol. 1, No. 4, pp. 66-73
NPL 2: Masamitsu Ichihashi, Masayuki Yagi, Keitaro Nomoto, and Yoshikazu Yonei, "Glycation Stress and Photo-Aging in Skin", Anti-Aging Medicine 8(3): 23-29, 2011
NPL 3: Satoshi Sato, "Changes in Dermal Extensibility and Contractility Associated with Aging", Journal of the Japan Geriatrics Society, July 1982, Vol. 19, No. 4, pp. 376-380

However, how skin is displaced greatly varies between individuals. Hence, even if the conventional technique is used, wrinkles that are highly likely to become existent in the near future (hereinafter, referred to as "potential wrinkles") cannot be detected accurately, which may result in performing unnecessary wrinkle care or result in not performing necessary wrinkle care. Accordingly, a technique that allows to efficiently care for potential wrinkles is sought for.

SUMMARY

Thus, a non-limiting exemplary embodiment of the present disclosure provides a wrinkle care support device and a method for supporting wrinkle care that allow to efficiently care for potential wrinkles. Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

In one general aspect, the techniques disclosed here feature: a wrinkle care support device including: a wrinkle change detector that detects a change made in a wrinkle after occurrence of the wrinkle in skin by provision of predetermined stimulation; a wrinkle care information determiner that determines, based on the detected change, user presentation information relating to the wrinkle care; and an information outputter that outputs the determined user presentation information.

These general and specific aspects may be implemented using a device, a system, a method, and a computer program, and any combination of devices, systems, methods, and computer programs.

According to the present disclosure, it is possible to efficiently care for potential wrinkles.

BRIEF DESCRIPTION OF THE DRAWINGS

FIG. 3 is a diagram showing an example of a wrinkle type table of the second exemplary embodiment;

FIG. 4 is a flowchart showing an example of operation of the wrinkle care support device according to the second exemplary embodiment;

FIG. 7 is a diagram showing an example of a configuration of a wrinkle care support device according to a third exemplary embodiment of the present disclosure;

FIG. 8 is a diagram showing an example of a wrinkle care table of the third exemplary embodiment;

FIG. 12 is a diagram showing an example of an evaluation table of the fourth exemplary embodiment;

FIG. 13 is a diagram showing an example of an additional wrinkle care table of the fourth exemplary embodiment;

DETAILED DESCRIPTION

Exemplary embodiments of the present disclosure will be described in detail below with reference to the drawings.

First Exemplary Embodiment

A first exemplary embodiment of the present disclosure is an example of a basic mode of the present disclosure.

Figure 1:
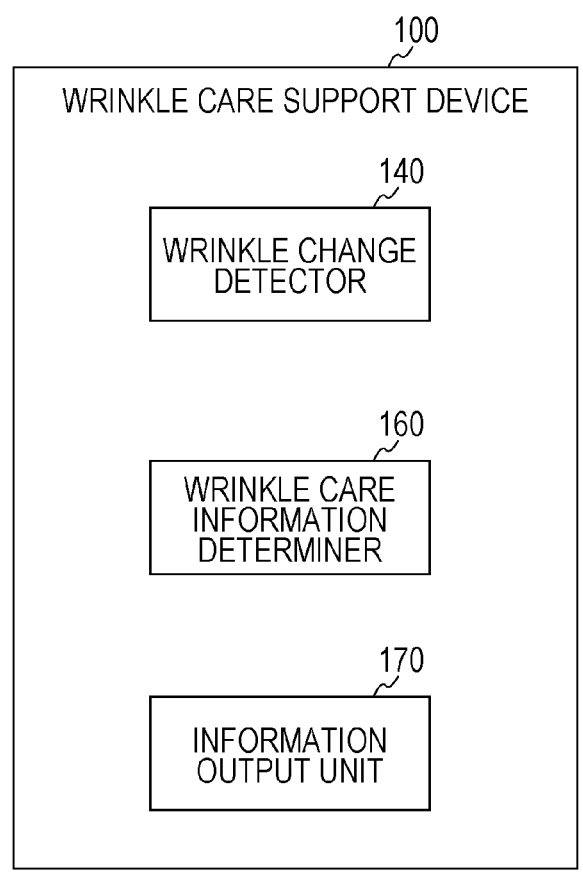
FIG. 1 is a diagram showing an example of a configuration of a wrinkle care support device according to a first exemplary embodiment of the present disclosure.

FIG. 1 is a block diagram showing an example of a configuration of a wrinkle care support device according to the present exemplary embodiment.

In FIG. 1, wrinkle care support device 100 includes wrinkle change detector 140, wrinkle care information determiner 160, and information output unit (outputter) 170.

Wrinkle change detector 140 detects a change made in a wrinkle after occurrence of the wrinkle, the wrinkle having occurred in skin by provision of predetermined stimulation.

Wrinkle care information determiner 160 determines, based on the detected change, information associated with whether the wrinkle is a potential wrinkle.

Information output unit 170 outputs the determined information to be presented to a user.

Note that, though not shown, wrinkle care support device 100 includes, for example, a CPU (Central Processing Unit), a storage medium such as a ROM (Read Only Memory) having stored therein a control program, and a work memory such as a RAM (Random Access Memory). In addition, though not shown, wrinkle care support device 100 includes, for example, a sensor device such as a camera that is required to detect a change in a wrinkle state; and an information output device such as a liquid crystal display that is required to output information. The operation of the sensor device and the information output device is controlled by the CPU. In this case, functions of the above-described components included in wrinkle care support device 100 are implemented by the CPU executing the control program.

Such wrinkle care support device 100 allows to efficiently care for potential wrinkles.

Second Exemplary Embodiment

A second exemplary embodiment of the present disclosure is an example of a specific mode of the present disclosure for a case of presenting types of wrinkles.

<For Types of Wrinkles>

Skin wrinkles include not only a wrinkle that can be always visually recognized (hereinafter, referred to as "existent wrinkle") and a wrinkle that can be temporarily visually recognized only when, for example, a facial expression is changed (hereinafter, referred to as "temporary wrinkle"), but also a wrinkle that is becoming an existent wrinkle but is normally not visually recognized (hereinafter, referred to as "potential wrinkle").

The potential wrinkle is normally not visually recognized and thus it is difficult to notice presence of the potential wrinkle. In addition, the potential wrinkle can be visually recognized if, for example, a facial expression is changed, but it is difficult to distinguish the potential wrinkle from the temporary wrinkle.

However, the temporary wrinkle and the potential wrinkle differ in their changes made after occurrence of the wrinkles. For example, when massage with fingers is performed on skin, a temporary wrinkle and a potential wrinkle appear on the skin. At this time, while displacement of the skin caused by the temporary wrinkle is significantly recovered in an instant, displacement of the skin caused by the potential wrinkle is recovered somewhat slowly.

This results from a fact that occurrence of a wrinkle is related to changes in mechanical properties such as a reduction in skin's strength and a reduction in skin's elasticity (see, for example, NPL 1 and NPL 2). In a condition of aged skin, i.e., a condition of skin where existent wrinkles are formed, since the skin's extensibility and contractility are reduced, contraction occurring after extension which is performed on a certain area tends to be delayed (see, for example, NPL 3).

In view of this, the wrinkle care support device according to the present exemplary embodiment determines, based on a change made in a wrinkle after occurrence of the wrinkle, whether the wrinkle is a potential wrinkle, and presents a result of the determination to a user, the wrinkle having occurred by massage performed on skin. Note that even if the wrinkle is a temporary wrinkle, it takes about one to two seconds to completely cancel out displacement of the skin caused by the wrinkle. Hence, how a wrinkle changes after occurrence of the wrinkle is sufficiently observable even from an image formed by a general moving-image camera.

<Configuration of the Device>

First, a configuration of the wrinkle care support device according to the present exemplary embodiment will be described.

Note that in the present exemplary embodiment the wrinkle care support device adopts a mode of a tablet terminal including a digital camera, a liquid crystal display with a touch panel, and a wireless communication circuit. Note also that a reduction target of the present exemplary embodiment is facial wrinkles of a user of the wrinkle care support device.

Figure 2:
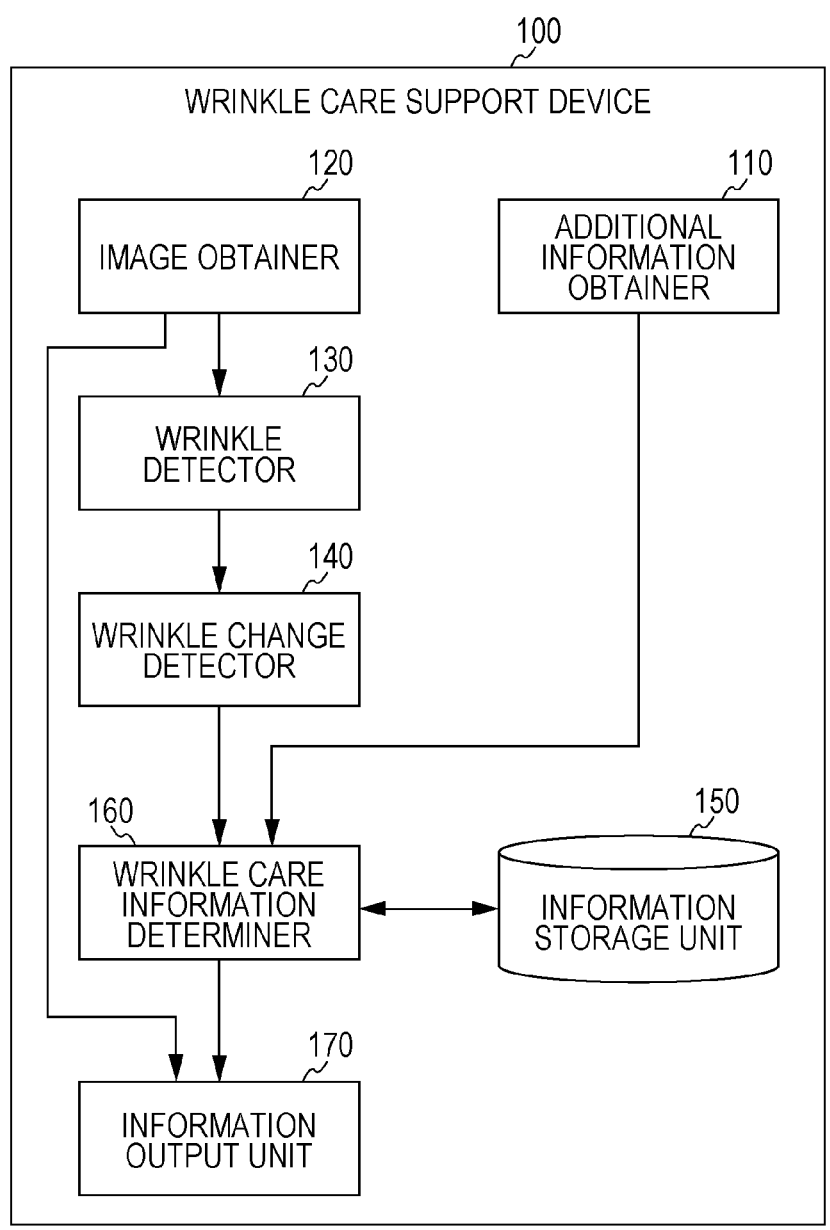
FIG. 2 is a diagram showing an example of a configuration of a wrinkle care support device according to a second exemplary embodiment of the present disclosure.

FIG. 2 is a block diagram showing an example of a configuration of the wrinkle care support device according to the present exemplary embodiment.

In FIG. 2, wrinkle care support device 100 includes additional information obtainer 110, image obtainer 120, wrinkle detector 130, wrinkle change detector 140, information storage unit 150, wrinkle care information determiner 160, and information output unit 170.

Additional information obtainer 110 obtains additional information including at least one of an age of a user (a person having skin), a temperature around the user, and a humidity around the user. More specifically, additional information obtainer 110 accepts input operations of additional information from the user through the above-described liquid crystal display with a touch panel. Alternatively, additional information obtainer 110 receives additional information by accessing a server placed on a communication network such as the Internet, through the above-described communication circuit. Then, additional information obtainer 110 outputs the obtained additional information to wrinkle care information determiner 160.

In the present exemplary embodiment, it is assumed that the additional information includes all of the age of the user (hereinafter, referred to as "user's age"), the temperature around the user, and the humidity around the user.

Image obtainer 120 obtains an image where a user's facial skin is photographed. More specifically, image obtainer 120 photographs video of a user's face at a frame rate (cycle) of 30 Hz to 60 Hz (hertz) through the above-described digital camera. Then, image obtainer 120 sequentially outputs frame images which form the photographed video to wrinkle detector 130. In addition, image obtainer 120 outputs a representative image of the video to information output unit 170. The representative image is, for example, an image photographed when the above-described massage starts.

Wrinkle detector 130 detects, for each input image, specific areas of the face from the image, and performs a process of detecting wrinkles (hereinafter, referred to as "wrinkle detection process") exclusively in the detected areas.

More specifically, wrinkle detector 130 detects, from an image, areas that are known to be likely to cause wrinkles, as the specific areas (hereinafter, referred to as "determination target areas"). Examples of the areas include outer corners of eyes, an area around lips, and areas around nasolabial folds. The detection is performed by publicly known image recognition processes, e.g., image pattern matching of facial parts such as eyes, a nose, and a mouth.

Then, wrinkle detector 130 detects wrinkles with levels higher than or equal to a predetermined level, in the input image exclusively in the detected determination target areas by publicly known wrinkle detection processes such as a technique described in PTL 2. Wrinkle detector 130 outputs, for each of the detected wrinkles, positional information indicating a relative position of the wrinkle relative to a facial part, to wrinkle change detector 140. Namely, pieces of information on presence of wrinkles with levels higher than or equal to the predetermined level which are obtained at respective times are sequentially input to wrinkle change detector 140.

Note that the level of wrinkles is a concept representing a strength of the wrinkles which is related to wrinkle depth, wrinkle width, wrinkle length, an amount of the wrinkles, a density of the wrinkles, and the like. Note also that the "wrinkle" in the following description indicates a wrinkle with a level higher than or equal to the predetermined level. Note also that the positional information of a wrinkle indicates a range of a wrinkle image area.

Wrinkle change detector 140 detects changes made in wrinkles after occurrence of the wrinkles, the wrinkles having occurred in the skin by provision of predetermined stimulation. More specifically, wrinkle change detector 140 monitors, for each determination target area, a wrinkle determination result while massage is performed on the user's face, and determines a period of time from when a wrinkle appearing by the massage is detected until the wrinkle is no longer detected (hereinafter, referred to as "wrinkle disappearing time"). Then, wrinkle change detector 140 outputs the wrinkle disappearing time for each determination target area to wrinkle care information determiner 160.

Note that wrinkle change detector 140 treats, for example, each of continuous, closed areas among wrinkle image areas, as an independent wrinkle. Note also that wrinkle change detector 140 treats, for example, wrinkles whose image areas overlap each other at a predetermined rate or more (e.g., 50% or more) between images with different photographing times, as an identical wrinkle.

In addition, when a wrinkle has not disappeared in a period of time which is a determination target, a length of the period of time which is the determination target serves as a wrinkle disappearing time of such a wrinkle. In addition, wrinkle change detector 140 calculates, for each determination target area, an average value of wrinkle disappearing times and uses the calculated value as a representative value of the wrinkle disappearing times for the determination target area.

Information storage unit 150 pre-stores wrinkle type tables. Each wrinkle type table includes a type of a wrinkle for each of the above-described wrinkle disappearing times. The type of a wrinkle serves as information about wrinkle care.

FIG. 3 is a diagram showing an example of a wrinkle type table.

As shown in FIG. 3, wrinkle type table 210 includes wrinkle type 213 for each combination of user's age 211 and wrinkle disappearing time 212.

For example, for a combination of user's age 211 "40s" and wrinkle disappearing time 212 "2-6 seconds", wrinkle type 213 "Potential" is provided. This indicates that in a case of a user in his/her 40s, a potential wrinkle has a wrinkle disappearing time of 2 seconds or more and less than 6 seconds, the wrinkle disappearing time being obtained when massage is performed.

Note that it is assumed that information storage unit 150 stores wrinkle type table 210 for each combination of a temperature around the user (hereinafter, simply referred to as "temperature") and a humidity around the user (hereinafter, simply referred to as "humidity"). This is because even if wrinkles are in the same state, wrinkle disappearing times of the wrinkles vary according to the temperature and humidity. Wrinkle type table 210 shown in FIG. 3 is an example case in which the temperature is 23° C. and the humidity is 50%.

In addition, such wrinkle type table 210 is created for combination patterns of various users' ages, temperatures, and humidities, based on experiments and empirical rules.

Wrinkle care information determiner 160 of FIG. 2 determines, for each determination target area, information about wrinkle care for reducing wrinkles detected in the area, by referring to wrinkle type table 210 (see FIG. 3) stored in information storage unit 150. More specifically, wrinkle care information determiner 160 considers a wrinkle type associated with pieces of content of the input additional information and a representative value of wrinkle disappearing times, as a wrinkle type of the detected wrinkles. Then, wrinkle care information determiner 160 outputs a result of the determination for each determination target area to information output unit 170.

Information output unit 170 outputs the input result of the determination for each determination target area through the liquid crystal display with a touch panel. More specifically, information output unit 170 creates an information display image by superimposing an image showing the result of the determination for each determination target area, on an input representative image. Then, information output unit 170 displays the created information display image on the liquid crystal display with a touch panel.

Note that, though not shown, wrinkle care support device 100 includes, for example, a CPU, a storage medium such as a ROM having stored therein a control program, and a work memory such as a RAM. Note also that operation of the above-described digital camera, liquid crystal display with a touch panel, and wireless communication circuit is controlled by, for example, the CPU. In this case, functions of the above-described components included in wrinkle care support device 100 are implemented by the CPU executing the control program.

Wrinkle care support device 100 having such a configuration can determine types of user's facial wrinkles based on wrinkle disappearing times obtained when massage is performed, and present results of the determination to the user or another person performing the massage.

<Operation of the Device>

Next, operation of wrinkle care support device 100 will be described.

FIG. 4 is a flowchart showing an example of operation of wrinkle care support device 100.

Note that here, for simplification of description, exemplification is made for operation performed when there is one determination target area and there is one wrinkle that can be detected from the area.

In step S1010, additional information obtainer 110 obtains user's additional information. Additional information to be obtained has, for example, pieces of content "user's age: 40s, temperature: 23° C., and humidity: 50%".

In step S1020, wrinkle change detector 140 instructs a user to start massage. Such an instruction is provided, for example, by displaying a guidance image showing how to perform massage, on the liquid crystal display with a touch panel.

In step S1030, image obtainer 120 photographs a user's face using the camera and thereby obtains a face image for one frame.

In step S1040, wrinkle detector 130 detects a determination target area from the obtained image.

In step S1050, wrinkle detector 130 performs a wrinkle detection process on the detected determination target area.

In step S1060, wrinkle change detector 140 determines whether a wrinkle has been detected from the determination target area. If a wrinkle has not been detected (S1060: NO), wrinkle change detector 140 proceeds to step S1070.

In step S1070, wrinkle change detector 140 determines whether ending of processing has been instructed by a user operation, etc. If ending of processing has not been instructed (S1070: NO), wrinkle change detector 140 returns to step S1030.

On the other hand, if a wrinkle has been detected (S1060: YES), wrinkle change detector 140 proceeds to step S1080. In addition, at this time, wrinkle change detector 140 starts clocking for detecting a wrinkle disappearing time. Note that wrinkles that can be detected here include an existent wrinkle that already appears even before performing the massage, in addition to a temporary wrinkle and a potential wrinkle that appear by the massage.

At steps S1080 to S1100, wrinkle care support device 100 performs the same processes as the processes at the above-described steps S1030 to S1050, on a next image.

In step S1110, wrinkle change detector 140 determines whether at least one of two conditions is satisfied. The two conditions include one that the wrinkle detected in step S1060 is no longer detected and another that elapsed time from step S1060 has reached a predetermined upper limit value and accordingly time limit is exceeded.

If the wrinkle is detected and the time limit is not exceeded (S1100: NO), wrinkle change detector 140 returns to step S1080. If the wrinkle is no longer detected or the time limit is exceeded (S1110: YES), wrinkle change detector 140 proceeds to step S1120. At this time, wrinkle change detector 140 obtains elapsed time from when the wrinkle is detected in step S1060, as a wrinkle disappearing time.

In step S1120, wrinkle care information determiner 160 determines a wrinkle type of the detected wrinkle by referring to wrinkle type table 210 (see FIG. 3) based on the additional information and the wrinkle disappearing time.

Then, in step S1130, information output unit 170 outputs an information display image showing a result of the determination, i.e., the determined wrinkle type.

Then, when the process in step S1130 is completed, wrinkle care support device 100 ends the series of processes.

In addition, if wrinkle change detector 140 determines that ending of processing has been instructed (S1070: YES), too, wrinkle care support device 100 ends the series of processes.

Note that when there are a plurality of wrinkles detected from the determination target area, wrinkle care support device 100 performs the processes at steps S1050 to S1110 for each wrinkle. Note also that when there are a plurality of determination target areas, wrinkle care support device 100 performs the process in step S1120 for each determination target area.

When there are a plurality of determination target areas, it is difficult to simultaneously massage all of the areas with fingers. Regarding this, by continuously detecting wrinkle disappearing times using wrinkle care support device 100 while the user changes a location where massage is performed, the user can sequentially check, for each of the plurality of determination target areas, a wrinkle type of a wrinkle present in the area.

In addition, since an image obtained during massage is used for detection of a wrinkle, there may be a case in which next massage operation starts before a determination is made as to whether a wrinkle having occurred by one massage operation has disappeared, the massage operation including, for example, sliding of fingers from corners of a mouth to temples. Namely, there may be a case in which next massage operation starts before maximum time for a temporary wrinkle to disappear or maximum time for a potential wrinkle to disappear has elapsed.

In this case, wrinkle care support device 100 redoes the processes at steps S1030 to S1130 (observation of a wrinkle) on a newly obtained frame image. Note that a determination as to be whether such a case has occurred can be made, for example, by determining whether a level of a wrinkle to be detected has increased before a maximum value of wrinkle disappearing times of potential wrinkles which are associated with the user's age has elapsed.

By such operation, wrinkle care support device 100 can detect a wrinkle disappearing time of a wrinkle present in a determination target area, determine a type of the wrinkle, and display the type of the wrinkle using an information display screen.

Figure 5:
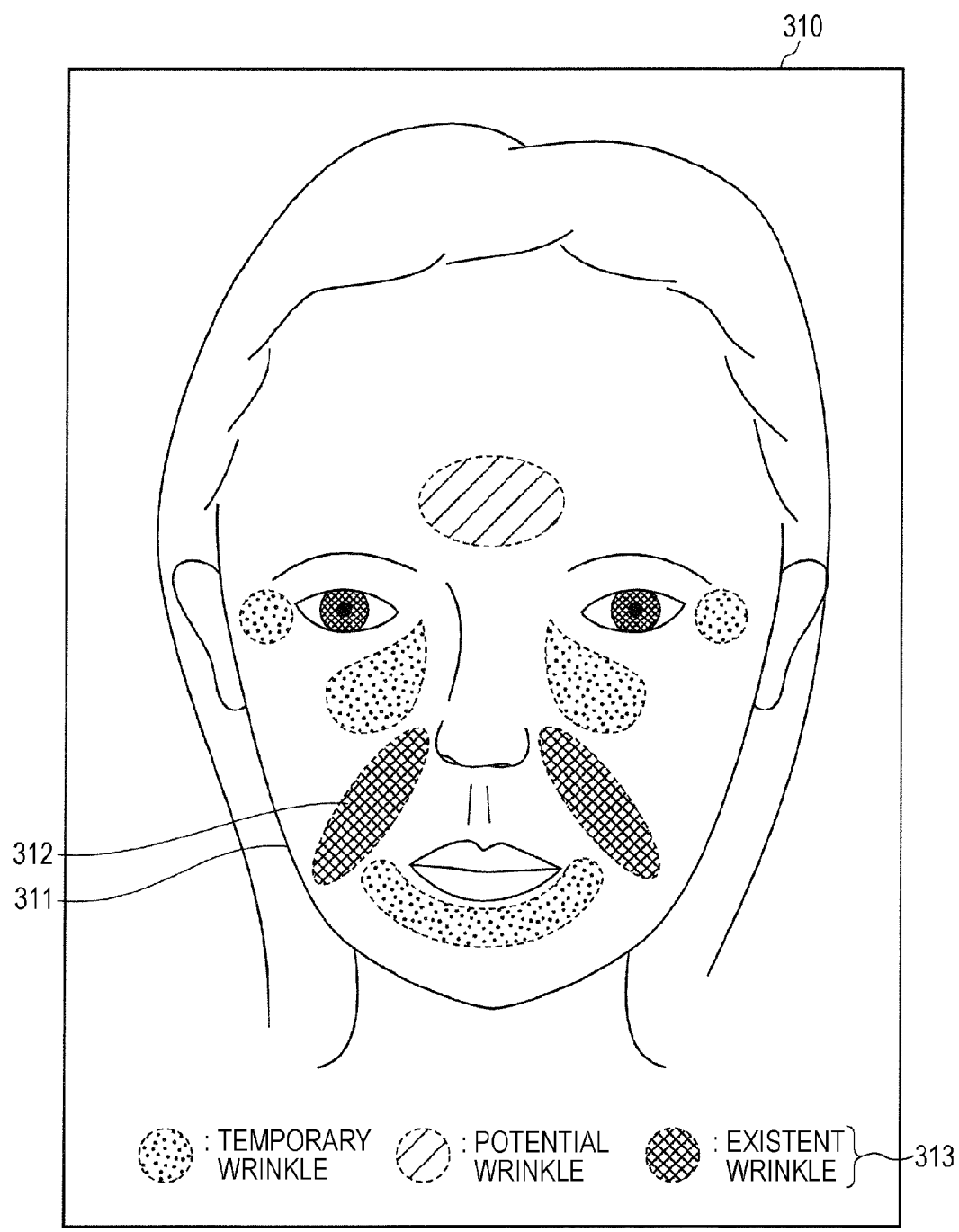
FIG. 5 is a diagram showing an example of an information display screen of the second exemplary embodiment.

FIG. 5 is a diagram showing an example of an information display screen to be output in step S1130 of FIG. 4. Note that exemplification is made for a case in which wrinkles are detected in a plurality of determination target areas.

As shown in FIG. 5, information display image 310 is displayed, for example, such that images 312 representing wrinkle types for the respective determination target areas are superimposed on user's face 311. In addition, information display image 310 includes description 313 of images 312 representing the wrinkle types.

For example, a determination target area between eyebrows has image 312 superimposed on the area. Image 312 shows presence of a potential wrinkle.

Therefore, by receiving presentation of such information display image 310, the user, who understands a relationship between wrinkle types and appropriate wrinkle care, can perform wrinkle care suitable for the potential wrinkle, on the part between the eyebrows.

Note that wrinkle care support device 100 may determine, for each wrinkle, a type of the wrinkle based on a wrinkle disappearing time of the wrinkle, and display results of the determination.

Figure 6:
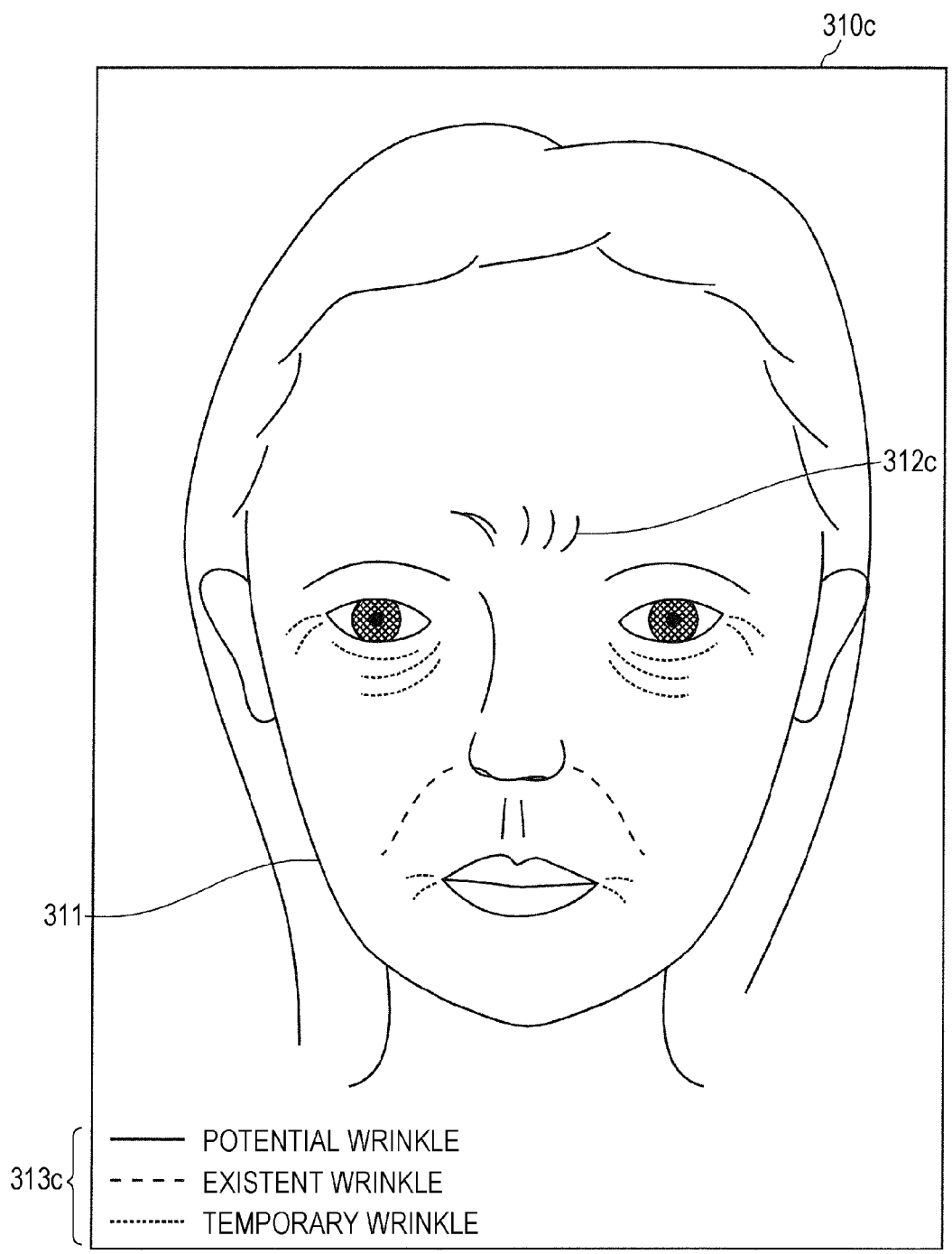
FIG. 6 is a diagram showing another example of an information display screen of the second exemplary embodiment.

FIG. 6 is a diagram showing another example of an information display screen and corresponds to FIG. 5.

As shown in FIG. 6, information display image 310c is displayed, for example, such that image 312c representing, for each wrinkle, a position, a shape, and a wrinkle type of the wrinkle is superimposed on user's face 311. In addition, information display image 310c includes description 313c of images 312c. Each image 312c is a linear image and represents different wrinkle types by, for example, different line types, different thicknesses, different colors, or different ways of blinking.

Note that, for wrinkle care for potential wrinkles, there is known effective care that includes, for example, an improvement in diet (optimal recipes and supplement of deficient nutrients), exercises for increasing muscle strength, a regular sleep schedule (by which activation of skin turnover can be expected), facial massage for blood circulation promotion and an improvement in metabolism, and protection against ultraviolet radiation. In addition, for wrinkle care for existent wrinkles, there is known effective care that includes, for example, moisturization by skin care products such as toners, moisturizers, and serums, supplement of effective components, intake of supplements or beauty drinks, facial massage, and prevention of dryness and sebum control by an improvement in a cleansing method.

Advantageous Effect of the Present Exemplary Embodiment

As described above, wrinkle care support device 100 according to the present exemplary embodiment detects a wrinkle disappearing time for when massage is performed on a face, determines a type of a wrinkle based on a length of the detected wrinkle disappearing time, and outputs a result of the determination. By this, wrinkle care support device 100 can notify a user of presence of potential wrinkles, and allows to efficiently care for the wrinkles.

Third Exemplary Embodiment

A third exemplary embodiment of the present disclosure is an example of a specific mode of the present disclosure for a case of presenting details of wrinkle care.

A wrinkle care support device according to the present exemplary embodiment determines details of appropriate wrinkle care based on a wrinkle disappearing time, and recommends the determined details of wrinkle care to a user.
<Configuration of a Device>

First, a configuration of the wrinkle care support device according to the present exemplary embodiment will be described.

FIG. 7 is a block diagram showing an example of a configuration of the wrinkle care support device according to the present exemplary embodiment, and corresponds to FIG. 2 of the second exemplary embodiment. The same portions as the portions in FIG. 2 are denoted by the same reference signs and description of those portions is omitted.

In FIG. 7, wrinkle care support device 100a includes information storage unit 150a, wrinkle care information determiner 160a, and information output unit 170a, instead of information storage unit 150, wrinkle care information determiner 160, and information output unit 170 of FIG. 2.

Note that those portions of the configuration of wrinkle care support device 100a other than information storage unit 150a, wrinkle care information determiner 160a, and information output unit 170a are the same as those of wrinkle care support device 100 of the second exemplary embodiment.

Information storage unit 150a pre-stores wrinkle care tables. Each wrinkle care table includes, for each of the above-described wrinkle disappearing times, details of wrinkle care suitable for a wrinkle of a type associated with the wrinkle disappearing time. The details of wrinkle care serve as information about wrinkle care.

FIG. 8 is a diagram showing an example of a wrinkle care table.

As shown in FIG. 8, wrinkle care table 220a includes, for each combination of user's age 221a and wrinkle disappearing time 222a, details of wrinkle care to be suggested to a user (hereinafter, referred to as "suggested care details") 223a.

For example, for a combination of user's age 221a "40s" and wrinkle disappearing time 222a "3-5 seconds", suggested care details 223a "Add moisturizers and supplements" are provided. This indicates that in a case of a user in his/her 40s, use of moisturizers and addition of supplements are effective for a wrinkle whose wrinkle disappearing time obtained when massage is performed is 3-5 seconds.

Note that although here simplified suggested care details 223a are shown and described, it is desirable that the details be more detailed and specific.

For example, in a case of a user in his/her 40s with a wrinkle disappearing time of 2-3 seconds, suggested care details 223a for wrinkle care by diet can include ingredients that improve skin metabolism, recipes using combinations of ingredients, amount and timing of food intake, etc. In addition, suggested care details 223a for wrinkle care by massage can include a guidance image or guidance video that explains a movement such as lifting fingers or a massage tool from a bottom to a top of a face, or explains how to perform massage taking into account blood circulation and lymph flow. Alternatively suggested care details 223a for wrinkle care by moisturizers and supplements can include information on products recommended to the user, which are statistically determined based on reviews and opinions by consumers having wrinkles of the same type (a level of wrinkles or a distribution of wrinkles) as the user.

In addition, it is assumed that information storage unit 150a stores wrinkle care tables 220a for each combination of a temperature and a humidity, as with wrinkle type tables 210 of the second exemplary embodiment. Wrinkle care table 220a shown in FIG. 8 is an example case in which the temperature is 23° C. and the humidity is 50%.

In addition, such wrinkle care table 220a is created for combination patterns of various users' ages, temperatures, and humidities, based on experiments and empirical rules.

Wrinkle care information determiner 160a of FIG. 7 determines suggested care details suitable for reducing wrinkles detected in each determination target area, by referring to wrinkle care table 220a (see FIG. 8) based on pieces of content of input additional information and a representative value of wrinkle disappearing times. Then, wrinkle care information determiner 160a outputs the determined suggested care details to information output unit 170a.

As with information output unit 170 of the second exemplary embodiment, information output unit 170a creates an information display image in which images showing results of the determination performed by wrinkle care information determiner 160a are superimposed on a representative image. Note, however, that an information display image to be created shows suggested care details but not wrinkle types.

Wrinkle care support device 100a having such a configuration can determine details of appropriate wrinkle care based on a wrinkle disappearing time obtained when massage is performed, and present the details to the user.

<Operation of the Device>

Next, operation of wrinkle care support device 100a will be described.

Figure 9:
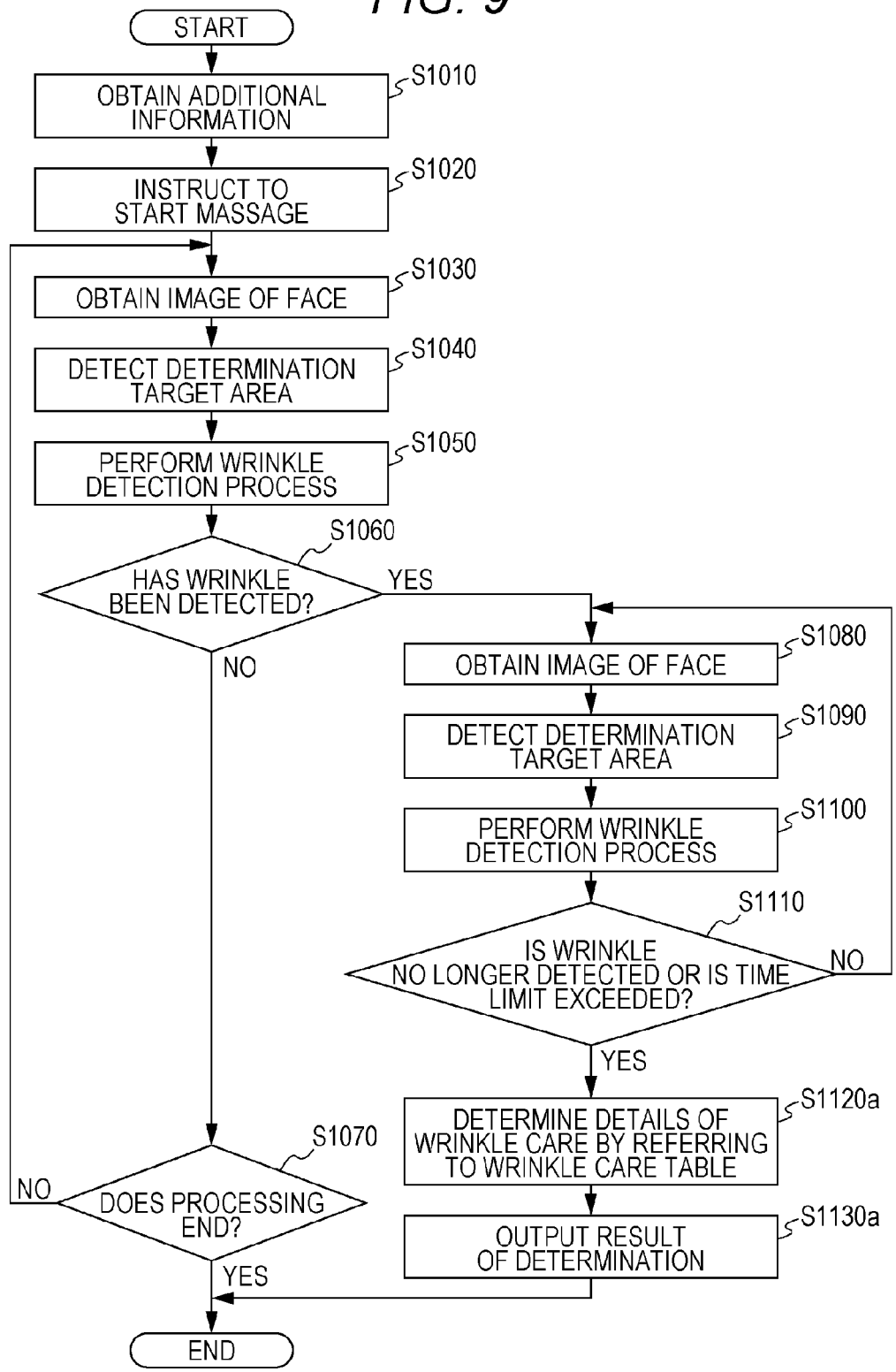
FIG. 9 is a flowchart showing an example of operation of the wrinkle care support device of the third exemplary embodiment.

FIG. 9 is a flowchart showing an example of operation of wrinkle care support device 100a, and corresponds to FIG. 4 of the second exemplary embodiment. The same portions as the portions in FIG. 4 are denoted by the same step numbers and description of those portions is omitted.

Processes at steps S1010 to S1110 are the same as the processes of the second exemplary embodiment. If wrinkle change detector 140 determines that a detected wrinkle is no longer detected or time limit is exceeded (S1110: YES), wrinkle change detector 140 proceeds to step S1120a.

In step S1120a, wrinkle care information determiner 160a determines suggested care details for the detected wrinkle, by referring to wrinkle care table 220a (see FIG. 8) based on additional information and a wrinkle disappearing time.

Then, in step S1130a, information output unit 170a outputs an information display image showing a result of the determination, i.e., the determined suggested care details.

By such operation, wrinkle care support device 100a can present details of specific wrinkle care to the user.

Figure 10:
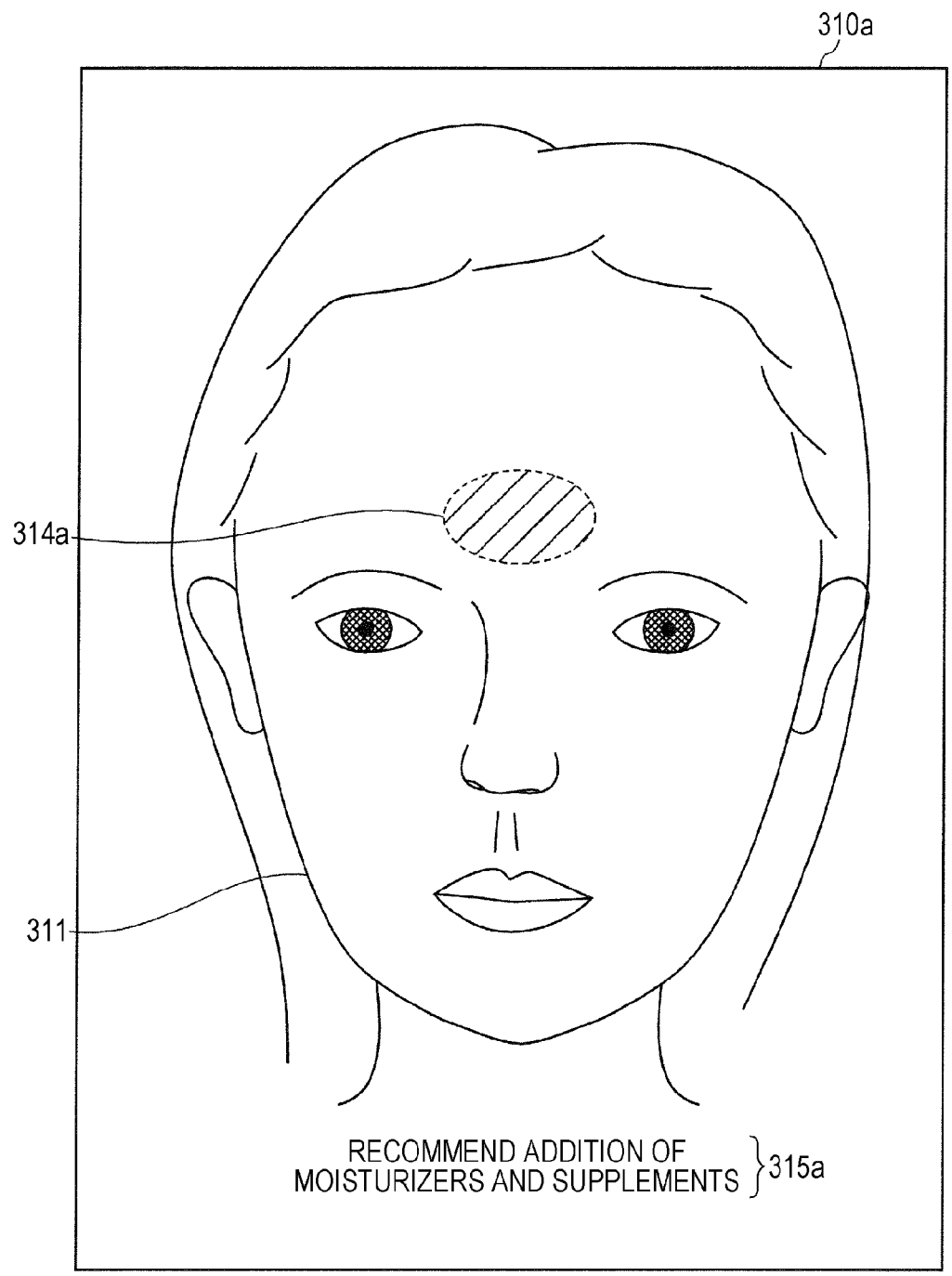
FIG. 10 is a diagram showing an example of an information display screen of the third exemplary embodiment.

FIG. 10 is a diagram showing an example of an information display screen to be output in step S1130a of FIG. 9, and corresponds to FIG. 5 of the second exemplary embodiment.

As shown in FIG. 10, information display image 310a is displayed, for example, such that image 314a representing an area where suggested care details are to be applied is superimposed on user's face 311. In addition, information display image 310a includes description 315a of the suggested care details to be applied to the area.

For example, image 314a is displayed in an area between eyebrows, and description 315a of suggested care details "Recommend addition of moisturizers and supplements" is displayed. By the presentation of such information display image 310a, the user can perform appropriate wrinkle care such as use of moisturizers and addition of supplements, as measures to reduce a wrinkle (including a potential wrinkle) in the part between the eyebrows.

Advantageous Effect of the Present Exemplary Embodiment

As described above, wrinkle care support device 100a according to the present exemplary embodiment detects a wrinkle disappearing time for when massage is performed on a face, determines details of appropriate wrinkle care based on a length of the detected wrinkle disappearing time, and outputs a result of the determination. By this, wrinkle care support device 100a can present, if there is a potential wrinkle, wrinkle care suitable for the wrinkle to a user, and allows to efficiently care for the potential wrinkle.

Namely, by using wrinkle care support device 100a according to the present exemplary embodiment, the user can promptly select and perform appropriate wrinkle care even if the user does not understand a relationship between wrinkle types and appropriate wrinkle care.

Fourth Exemplary Embodiment

A fourth exemplary embodiment of the present disclosure is an example of a specific mode of the present disclosure for a case of further evaluating presented wrinkle care.

Even if wrinkle care of the same details is performed on wrinkles of the same type and the same strength, a wrinkle reduction effect varies between individuals. In addition, a state of implementation of suggested wrinkle care also varies between individuals. In view of this, a wrinkle care support device according to the present exemplary embodiment detects a wrinkle disappearing time again after suggesting wrinkle care to a user, and evaluates an effect of the suggested wrinkle care.

<Configuration of the Device>

First, a configuration of the wrinkle care support device according to the present exemplary embodiment will be described.

Figure 11:
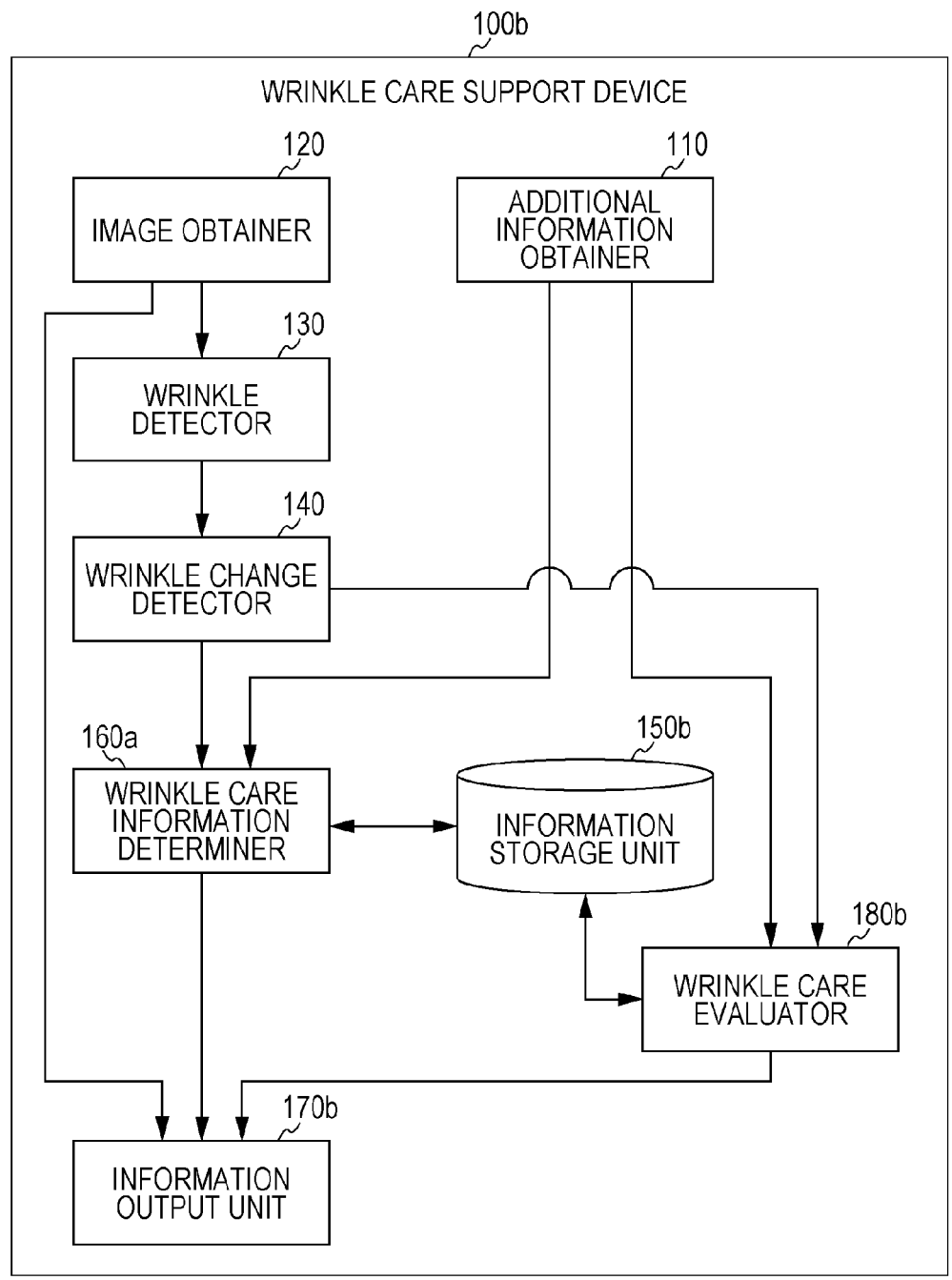
FIG. 11 is a diagram showing an example of a configuration of a wrinkle care support device according to a fourth exemplary embodiment of the present disclosure.

FIG. 11 is a block diagram showing an example of a configuration of the wrinkle care support device according to the present exemplary embodiment, and corresponds to FIG. 7 of the third exemplary embodiment. The same portions as the portions in FIG. 7 are denoted by the same reference signs and description of those portions is omitted.

In FIG. 11, wrinkle care support device 100b includes information storage unit 150b and information output unit 170b, instead of information storage unit 150a and information output unit 170a of FIG. 7, and further includes wrinkle care evaluator 180b.

Note that those portions of the configuration of wrinkle care support device 100b other than information storage unit 150b, information output unit 170b, and wrinkle care evaluator 180b are the same as those of wrinkle care support device 100a of the third exemplary embodiment. Note, however, that additional information obtainer 110 and wrinkle change detector 140 output additional information and wrinkle disappearing times not only to wrinkle care information determiner 160a but also to wrinkle care evaluator 180b.

Information storage unit 150b pre-stores evaluation tables and additional wrinkle care tables in addition to wrinkle care tables 220a (see FIG. 8). Each evaluation table includes, for each wrinkle disappearing time obtained after suggested care details are performed, whether the wrinkle care is sufficiently effective. Each additional wrinkle care table includes, for each wrinkle disappearing time obtained before suggested care details are performed, details of wrinkle care to be performed when an effect of the suggested care details is insufficient.

Note that, in the following description, "before suggested care details are performed" is referred to as "pre-care", and "after the suggested care details are performed" is referred to as "post-care".

FIG. 12 is a diagram showing an example of an evaluation table.

As shown in FIG. 12, evaluation table 230b includes determination 234b as to whether suggested care details presented to a user are sufficiently effective, for each combination of user's age 231b, pre-care wrinkle disappearing time 232b, and reduction rate 233b of a post-care wrinkle eliminating time.

Note that, when the pre-care wrinkle disappearing time is represented by T0 and the post-care wrinkle eliminating time is represented by T, reduction rate 233b of a wrinkle eliminating time is represented by, for example, (T−T0)/T0. Reduction rate 233b of a wrinkle eliminating time namely indicates a degree of improvement in a wrinkle state.

For example, for a combination of user's age 231b "40s", pre-care wrinkle disappearing time 232b "3-5 seconds", and reduction rate 233b of a post-care wrinkle eliminating time "less than 20%", determination 234b "Not effective" is provided. This indicates that in a case of a user in his/her 40s, when the pre-care wrinkle disappearing time is 3-5 seconds and the reduction rate of a post-care wrinkle eliminating time is less than 20%, an effect of wrinkle care by suggested care details has been insufficient.

FIG. 13 is a diagram showing an example of an additional wrinkle care table.

As shown in FIG. 13, additional wrinkle care table 240b includes, for each combination of user's age 241b and pre-care wrinkle disappearing time 242b, details of next care for a case in which wrinkle care is not effective (hereinafter, referred to as "additional suggested care details") 243b.

For a combination of user's age 241b "40s" and pre-care wrinkle disappearing time 242b "3-5 seconds", additional suggested care details 243b "Add muscle strengthening and protection against ultraviolet radiation" are provided. This indicates that in a case of a user in his/her 40s, if the pre-care wrinkle disappearing time is 3-5 seconds and an effect of wrinkle care by suggested care details is insufficient, then it is effective to add muscle strengthening and protection against ultraviolet radiation in addition to the wrinkle care by the suggested care details.

Note that it is assumed that information storage unit 150b of FIG. 11 stores evaluation tables 230b and additional wrinkle care tables 240b for each combination of a temperature and a humidity, as with wrinkle care tables 220a of the third exemplary embodiment. Evaluation table 230b shown in FIG. 12 and additional wrinkle care table 240b shown in FIG. 13 are an example case in which the temperature is 23° C. and the humidity is 50%.

In addition, such evaluation table 230b and additional wrinkle care table 240b are created for combination patterns of various users' ages, temperatures, and humidities, based on experiments and empirical rules.

Information output unit 170b of FIG. 11 creates and displays different information display images for two different modes: wrinkle care selection mode and wrinkle care evaluation mode. In the wrinkle care selection mode, information output unit 170b displays an image presenting suggested care details, which is the same as information display image 310a (see FIG. 10) described in the third exemplary embodiment. In the wrinkle care evaluation mode, information output unit 170b displays an image presenting additional suggested details determined by wrinkle care evaluator 180b which will be described later.

Note that switching between wrinkle care selection mode and wrinkle care evaluation mode may be performed by any of the device components included in wrinkle care support device 100b such as image obtainer 120, based on elapsed time from when suggested care details are presented (e.g., one week), or in response to a user operation.

In the wrinkle care selection mode, wrinkle care evaluator 180b stores a wrinkle disappearing time for each determination target area which is input before care, in information storage unit 150b.

In addition, in the wrinkle care evaluation mode, wrinkle care evaluator 180b evaluates effectiveness of wrinkle care based on a wrinkle disappearing time detected before care and a wrinkle eliminating time input after the care, the wrinkle care being supposed to have been performed based on suggested care details.

More specifically, wrinkle care evaluator 180b determines, for each determination target area, whether suggested care details are sufficiently effective, by referring to evaluation table 230b (see FIG. 12) stored in information storage unit 150b, based on the above-described reduction rate of a post-care wrinkle eliminating time. If wrinkle care evaluator 180b determines that the effect is insufficient, wrinkle care evaluator 180b determines additional suggested care details to be presented to the user, by referring to additional wrinkle care table 240b (see FIG. 13) stored in information storage unit 150b, based on a user's age and a pre-care wrinkle disappearing time.

Then, wrinkle care evaluator 180b outputs the determined additional suggested care details to information output unit 170b.

In the wrinkle care selection mode, information output unit 170b performs the same operation as information output unit 170a of the third exemplary embodiment. In addition, in the wrinkle care evaluation mode, information output unit 170b creates and displays an information display image in which images showing results of the determination performed by wrinkle care evaluator 180b are superimposed on a representative image.

Wrinkle care support device 100b having such a configuration can evaluate effectiveness of wrinkle care suggested to a user and suggest, if necessary, wrinkle care to be performed additionally to the user.

<Operation of the Device>

Next, operation of wrinkle care support device 100b will be described.

Figure 14:
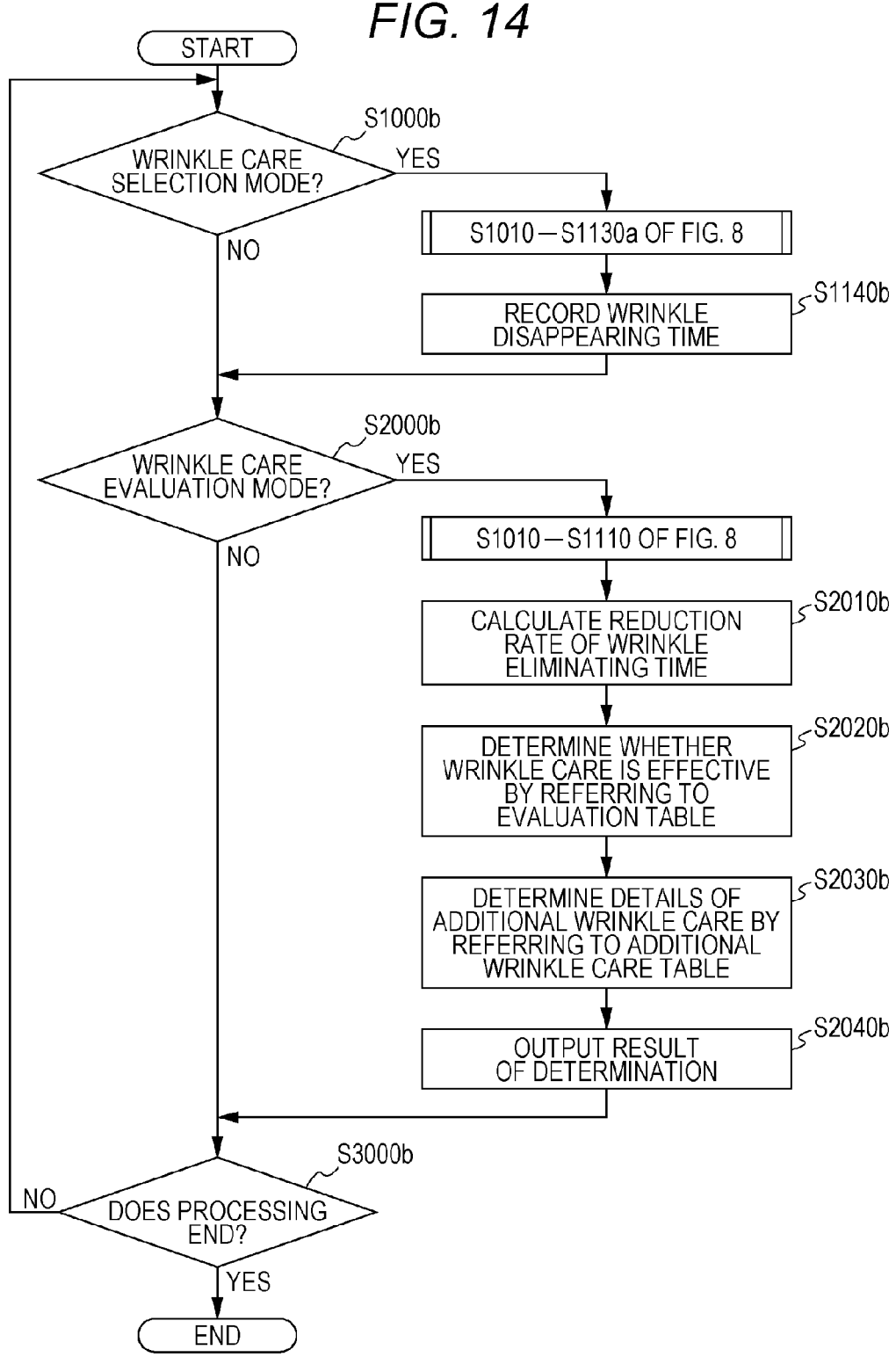
FIG. 14 is a flowchart showing an example of operation of the wrinkle care support device according to the fourth exemplary embodiment.

FIG. 14 is a flowchart showing an example of operation of wrinkle care support device 100b, and corresponds to FIG. 9 of the third exemplary embodiment. The same portions as the portions in FIG. 9 are denoted by the same step numbers and description of those portions is omitted.

In step S1000b, for example, image obtainer 120 determines whether wrinkle care support device 100b is in the wrinkle care selection mode. If wrinkle care support device 100b is not in the wrinkle care selection mode (S1000b: NO), wrinkle care support device 100b proceeds to step S2000b which will be described later.

If wrinkle care support device 100b is in the wrinkle care selection mode (S1000b: YES), wrinkle care support device 100b performs the processes at steps S1010 to S1130a of FIG. 9, and proceeds to step S1140b. Namely, wrinkle care support device 100b suggests details of wrinkle care to be performed on a user's facial wrinkle.

In step S1140b, wrinkle care evaluator 180b records a pre-care wrinkle disappearing time for each determination target area, in information storage unit 150b.

In step S2000b, for example, image obtainer 120 determines whether wrinkle care support device 100b is in the wrinkle care evaluation mode. If wrinkle care support device 100b is not in the wrinkle care evaluation mode (S2000b: NO), wrinkle care support device 100b proceeds to step S3000b which will be described later.

If wrinkle care support device 100b is in the wrinkle care evaluation mode (S2000b: YES), wrinkle care support device 100b performs the processes at steps S1010 to S1110 of FIG. 9, and proceeds to step S2010b. Namely, wrinkle care support device 100b obtains additional information and detects a post-care wrinkle eliminating time for each determination target area.

In step S2010b, wrinkle care evaluator 180b calculates a reduction rate of a wrinkle eliminating time, based on the pre-care wrinkle disappearing time and the post-care wrinkle eliminating time.

In step S2020b, wrinkle care evaluator 180b determines whether the wrinkle care is effective, by referring to evaluation table 230b (see FIG. 12) based on the additional information and the calculated reduction rate of a wrinkle eliminating time.

In step S2030b, wrinkle care evaluator 180b determines additional suggested care details for a case in which the wrinkle care has not been effective (small effect), by referring to additional wrinkle care table 240b (see FIG. 13).

Note, however, that when the wrinkle care has been effective (large effect), wrinkle care evaluator 180*b* does not need to perform such a determination.

In step S2040*b*, wrinkle care evaluator 180*b* outputs a result of the determination. More specifically, when wrinkle care evaluator 180*b* determines that the wrinkle care has been effective, wrinkle care evaluator 180*b* creates and displays an information display image showing that the wrinkle care has been effective or that the suggested care details should be continued. When wrinkle care evaluator 180*b* determines that the wrinkle care has not been effective, wrinkle care evaluator 180*b* creates and displays an information display image showing additional suggested care details.

Then, in step S3000*b*, for example, image obtainer 120 determines whether wrinkle care support device 100*b* is instructed to end a process for wrinkle care, by a user operation, etc. If wrinkle care support device 100*b* is not instructed to end the process (S3000*b*: NO), wrinkle care support device 100*b* returns to step S1000*b* and repeats a mode determination. If wrinkle care support device 100*b* is instructed to end the process (S3000*b*: YES), wrinkle care support device 100*b* ends the series of processes.

By such operation, wrinkle care support device 100*b* can evaluate suggested care details based on whether the suggested care details are effective, and suggest, if necessary, additional suggested care details to the user.

Figure 15:
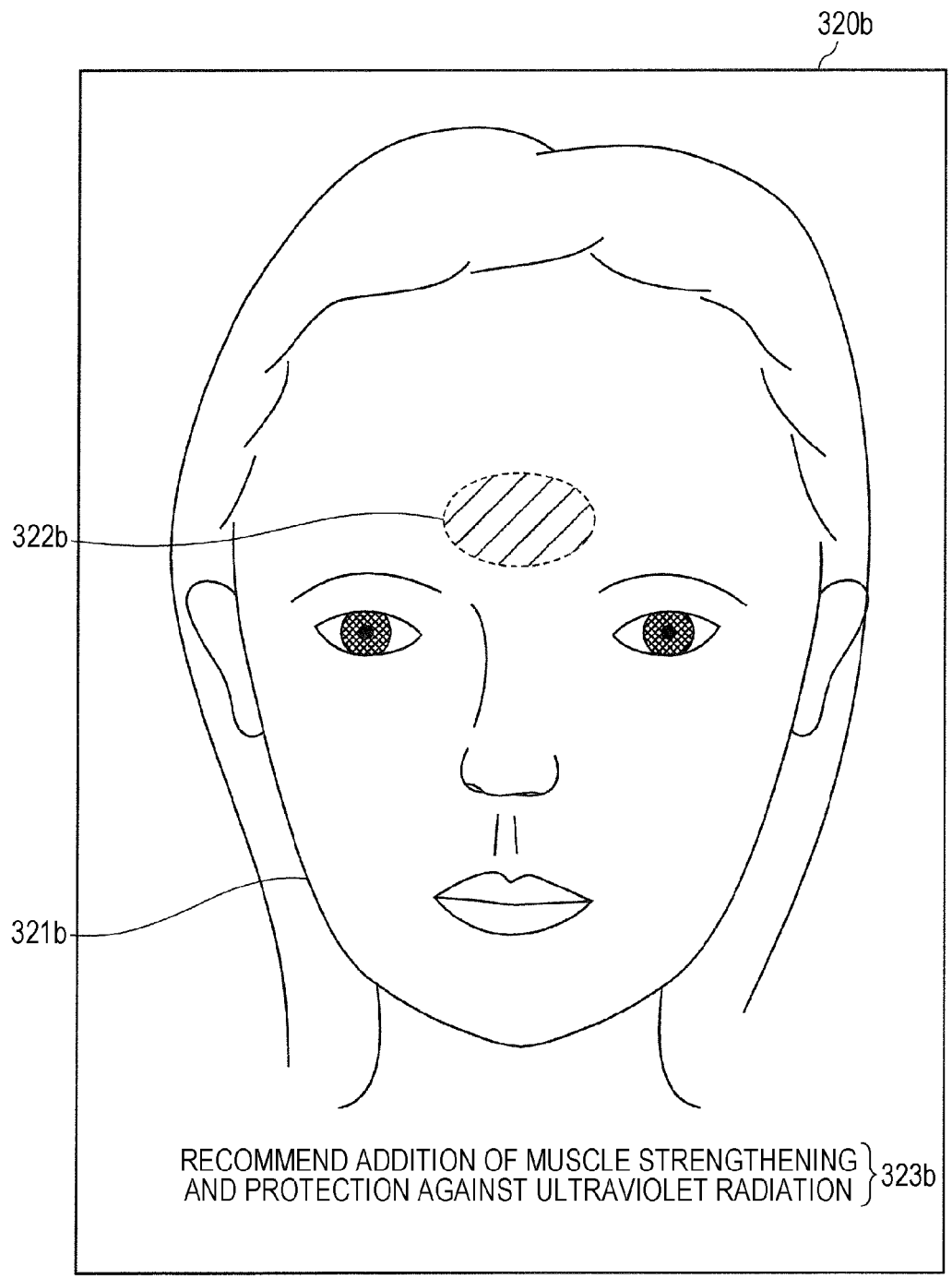
FIG. 15 is a diagram showing an example of an information display screen of the fourth exemplary embodiment.

FIG. 15 is a diagram showing an example of an information display screen to be output in step S2040*b* of FIG. 14, and corresponds to FIG. 10 of the third exemplary embodiment.

As shown in FIG. 15, information display image 320*b* is displayed, for example, such that image 322*b* representing an area where additional suggested care details are to be applied is superimposed on user's face 321*b*. In addition, information display image 320*b* includes description 323*b* of the additional suggested care details to be applied to the area.

For example, image 322*b* is displayed in an area between eyebrows, and description 323*b* of additional suggested care details "Recommend addition of muscle strengthening and protection against ultraviolet radiation" is displayed. By the presentation of such information display image 320*b*, the user can perform wrinkle care suitable for a wrinkle, such as addition of muscle strengthening and protection against ultraviolet radiation, as new measures to reduce the wrinkle (including a potential wrinkle) in the part between the eyebrows.

Note that after wrinkle care support device 100*b* has suggested wrinkle care once, wrinkle care support device 100*b* may periodically repeat only wrinkle care evaluation mode. In this case, in the wrinkle care evaluation mode, too, wrinkle care support device 100*b* records a wrinkle disappearing time for each determination target area, and treats the wrinkle disappearing time as a pre-care wrinkle disappearing time in next evaluation. By this, wrinkle care support device 100*b* can continuously suggest details of optimal wrinkle care whenever necessary.

Advantageous Effects of the Present Exemplary Embodiment

As described above, wrinkle care support device 100*b* according to the present exemplary embodiment detects a change in a wrinkle disappearing time between before and after wrinkle care which is suggested to a user, evaluates an effect of the wrinkle care based on the detected change in a wrinkle disappearing time, and outputs a result of the evaluation. By this, when the wrinkle care has a small effect, wrinkle care support device 100*b* can notify the user of such a fact and encourage the user to select more appropriate wrinkle care.

In addition, when the wrinkle care has a small effect, wrinkle care support device 100*b* according to the present exemplary embodiment presents appropriate additional suggested care details to the user, based on a pre-care wrinkle disappearing time. By this, when the wrinkle care has a small effect, wrinkle care support device 100*b* can specifically suggest more appropriate wrinkle care to the user.

Namely, even when there are variations in an effect of wrinkle care, wrinkle care support device 100*b* according to the present exemplary embodiment allows the user to efficiently care for potential wrinkles.

Note that wrinkle care support device 100*b* may present only an evaluation result of suggested care details to the user. In this case, the user can, for example, determine whether to continue the suggested care details.

Variants of Each Exemplary Embodiment

Note that a target of wrinkle care suggested by a wrinkle care support device according to each exemplary embodiment described above is not limited to the above-described example. The target of wrinkle care may be, for example, skin of other portions of a body such as a neck and a stomach area.

In addition, the predetermined stimulation performed on skin to determine a change in a wrinkle state is not limited to the above-described example (massage). The stimulation may be any stimulation as long as the stimulation allows at least a potential wrinkle to appear on skin as a wrinkle that is detectable by, for example, an image sensor. For example, the stimulation may be pinching, pulling, or compression of skin or may be a change in a facial expression.

For example, the wrinkle care support device may instruct a user, by an image or audio, to make a plurality of predetermined facial expressions, such as a smiling face, a confused face, a crying face, and an angry face, and detect a wrinkle state for each facial expression. Then, the wrinkle care support device may perform an overall analysis of results of the detection for the facial expressions, and detect (determine) potential wrinkles. For such an analysis, a statistical process can be used. Namely, the wrinkle care support device performs, for example, an analysis for the type of wrinkle state about which portions are likely to increase wrinkles in the future, and then presents a possibility of potential wrinkles to a user.

In addition, a change in a wrinkle state occurring when the above-described stimulation is performed is not limited to the above-described example (wrinkle disappearing time), the change being a target of detection performed by the wrinkle care support device according to each exemplary embodiment. The change in a wrinkle state may be, for example, a change in a level of a wrinkle obtained at a point in time when a predetermined period of time has elapsed from occurrence of the wrinkle (e.g., 3 seconds later).

In addition, the wrinkle care support device according to each exemplary embodiment may achieve an improvement (reinforcement) in accuracy of wrinkle type determination, based on information other than a change in a wrinkle state. For example, states of a human skeleton and sinews are correlated with a condition of skin. Therefore, the wrinkle care information determiner may obtain information about states of user's skeleton and sinews, which is obtained by, for example, MRI (Magnetic Resonance Imaging) or CT (Computed Tomography), and determine wrinkle types based on the information.

In addition, information associated with whether a wrinkle is not limited to the above-described examples (wrinkle type or details of wrinkle care), the information being a target of determination and output performed by the wrinkle care support device according to each exemplary embodiment. The information may be, for example, a level of a wrinkle or a degree of necessity of wrinkle care.

In addition, a unit of determination performed by the wrinkle care support device according to each exemplary embodiment is not limited to the above-described example (determination target areas). Such a determination may be performed, for example, in units of blocks into which an entire skin part is divided minutely or units of each individual wrinkle.

In addition, the wrinkle care support device according to each exemplary embodiment may make a determination on wrinkle types and a determination on details of appropriate wrinkle care, targeting only potential wrinkles. This is because temporary wrinkles are low in necessity of wrinkle care, and existent wrinkles are easily recognized by a user him/herself.

In addition, potential wrinkles may be classified into a plurality of subdivided wrinkle types, according to a wrinkle disappearing time or a level of a wrinkle. In addition, in this case, it is desirable that the wrinkle care support device according to the second exemplary embodiment determine suggested care details, using a table including the subdivided wrinkle types and suggested care details associated with the respective subdivided wrinkle types.

In addition, a part of a configuration of the wrinkle care support device according to each exemplary embodiment may be physically separated from other portions of the configuration of the wrinkle care support device. In this case, those configurations each need to include a communicator for performing communication with each other.

Summary of the Present Disclosure

A wrinkle care support device of the present disclosure includes: a wrinkle change detector that detects a change made in a wrinkle after occurrence of the wrinkle, the wrinkle having occurred in skin by provision of predetermined stimulation; a wrinkle care information determiner that determines, based on the detected change, information associated with whether the wrinkle is a potential wrinkle; and an information output unit that outputs the determined information.

Note that the above-described wrinkle care support device may include an image obtainer that obtains an image where the skin is photographed; and a wrinkle detector that detects the wrinkle from the obtained image, and the change may include a wrinkle disappearing time starting from when the wrinkle appearing by the provision of the predetermined stimulation is detected until the wrinkle is no longer detected.

In addition, the above-described wrinkle care support device may include an information storage unit that pre-stores a table including wrinkle disappearing times and pieces of information about wrinkle care associated with the respective wrinkle disappearing times, and the wrinkle care information determiner may determine a piece of information about wrinkle care associated with a detected wrinkle disappearing time, by referring to the table.

In addition, the above-described wrinkle care support device may include an additional information obtainer that obtains additional information including at least one of an age of a person having the skin, a temperature around the skin, and a humidity around the skin, the table may include pieces of content of the additional information and the pieces of information about wrinkle care associated with the respective pieces of content of the additional information, and the wrinkle care information determiner may determine a piece of information associated with the obtained additional information, by referring to the table.

In addition, in the above-described wrinkle care support device, the pieces of information about wrinkle care may include types of the wrinkle, and the types of the wrinkle may include at least a potential wrinkle.

In addition, in the above-described wrinkle care support device, the pieces of information about wrinkle care may include details of the wrinkle care, and the details of the wrinkle care may include at least details of wrinkle care suitable for a potential wrinkle.

In addition, in the above-described wrinkle care support device, the wrinkle detector may detect a specific area of a face from the obtained image, and detect the wrinkle exclusively in the detected area.

In addition, the above-described wrinkle care support device may include a wrinkle care evaluator that evaluates effectiveness of wrinkle care based on a wrinkle disappearing time detected before the information is output and a wrinkle disappearing time detected after the information is output, the wrinkle care being supposed to have been performed based on the output information.

In addition, in the above-described wrinkle care support device, the predetermined stimulation may include skin massage with fingers.

A method for supporting wrinkle care of the present disclosure includes the steps of: detecting a change made in a wrinkle after occurrence of the wrinkle, the wrinkle having occurred in skin by provision of predetermined stimulation; determining, based on the detected change, information associated with whether the wrinkle is a potential wrinkle; and outputting the determined information.

Note that although, in each the above-described exemplary embodiments, a wrinkle care support device is described as a tablet terminal including a digital camera, a liquid crystal display with a touch panel, and a wireless communication circuit, the wrinkle care support device may be a so-called electronic mirror device that is used as a mirror by displaying, on a display, an image photographed by a camera. In this case, a display unit (mirror) may adopt a mode of another device that displays images, etc., by communicating with an information output unit of the wrinkle care support device. In addition, the electronic mirror device may be a device capable of switching between an image display state and a mirror state, or may be a device that performs display such that information or the like generated by the wrinkle care support device is superimposed on the mirror.

The present disclosure is effective as a wrinkle care support device and a method for supporting wrinkle care that allow to efficiently care for potential wrinkles.

What is claimed is:
1. A wrinkle care support device comprising:
a memory that stores instructions; and
a processor that, when executing the instructions stored in the memory, performs operations comprising:

obtaining an image where skin is photographed;
detecting a wrinkle in the skin from the obtained image, the wrinkle appearing in response to predetermined stimulation;
obtaining time-sequential images of the wrinkle after an appearance of the wrinkle in response to the predetermined stimulation;
detecting a wrinkle disappearing time, which is an elapsed time from the appearance of the wrinkle in response to the predetermined stimulation to a disappearance of the wrinkle, based on the obtained time-sequential images;
determining wrinkle care user presentation information corresponding to the detected wrinkle disappearing time; and
outputting the determined wrinkle care user presentation information.

2. The wrinkle care support device according to claim 1, wherein the memory further stores a table including wrinkle disappearing times and wrinkle care information associated with the respective wrinkle disappearing times, and
the processor further determines wrinkle care information based on the detected wrinkle disappearing time, by referring to the table.

3. The wrinkle care support device according to claim 2, wherein the processor further obtains additional information including at least one of an age of a person having the skin, a temperature, or a humidity,
wherein the table further includes the additional information associated with the respective wrinkle care information, and
wherein the processor determines the wrinkle care information based on the obtained additional information, by referring to the table.

4. The wrinkle care support device according to claim 2, wherein the wrinkle care information includes types of wrinkles, and
wherein the types of wrinkles include a potential wrinkle type.

5. The wrinkle care support device according to claim 2, wherein the wrinkle care information includes a wrinkle care suggestion for a potential wrinkle type.

6. The wrinkle care support device according to claim 1, wherein the processor detects a specific area of a face from the obtained image, and detects the wrinkle in the detected specific area.

7. The wrinkle care support device according to claim 1, wherein the processor evaluates effectiveness of wrinkle care based on the wrinkle disappearing time detected before the wrinkle care user presentation information is output and a wrinkle disappearing time detected after the wrinkle care user presentation information is output.

8. The wrinkle care support device according to claim 1, wherein the predetermined stimulation includes stimulation to displace the skin.

9. The wrinkle care support device according to claim 1, wherein the processor further creates an information display image by superimposing an image relating to a wrinkle care on a user representative image based on the determined wrinkle care user presentation information, and displays the created information display image.

10. A computer-implemented method for supporting wrinkle care, the method comprising:
obtaining, by a processor, an image where skin is photographed;
detecting, by a processor, a wrinkle in the skin from the obtained image, the wrinkle appearing in response to predetermined stimulation;
obtaining, by a processor, time-sequential images of the wrinkle after an appearance of the wrinkle in response to the predetermined stimulation;
detecting, by a processor, a wrinkle disappearing time, which is an elapsed time from the appearance of the wrinkle in response to the predetermined stimulation to a disappearance of the wrinkle, based on the obtained time-sequential images;
determining, by a processor, wrinkle care user presentation information corresponding to the detected wrinkle disappearing time; and
outputting, by a processor, the determined wrinkle care user presentation information.

11. The computer-implemented method for supporting wrinkle care according to claim 10, wherein a table is stored in a memory, the table including wrinkle disappearing times and wrinkle care information associated with the respective wrinkle disappearing times,
the method further comprising determining wrinkle care information based on the detected wrinkle disappearing time, by referring to the table.

12. The computer-implemented method for supporting wrinkle care according to claim 11, further comprising obtaining, by a processor, additional information including at least one of an age of a person having the skin, a temperature, or a humidity;
wherein the table further includes the additional information associated with the respective wrinkle care information, and
wherein the method further comprising determining, by a processor, the wrinkle care information based on the obtained additional information, by referring to the table.

13. The computer-implemented method for supporting wrinkle care according to claim 11,
wherein the wrinkle care information includes types of wrinkles, and
wherein the types of wrinkles include a potential wrinkle type.

14. The computer-implemented method for supporting wrinkle care according to claim 11,
wherein the wrinkle care information includes a wrinkle care suggestion for a potential wrinkle type.

15. The computer-implemented method for supporting wrinkle care according to claim 10, further comprising:
detecting a specific area of a face from the obtained image; and
detecting the wrinkle in the detected specific area.

16. The computer-implemented method for supporting wrinkle care according to claim 10, further comprising evaluating effectiveness of a wrinkle care based on the wrinkle disappearing time detected before the wrinkle care user presentation information is output and a wrinkle disappearing time detected after the wrinkle care user presentation information is output.

17. The computer-implemented method for supporting wrinkle care according to claim 10, wherein the predetermined stimulation includes stimulation to displace the skin.

18. The computer-implemented method for supporting wrinkle care according to claim 10, further comprising:
creating, by a processor, an information display image by superimposing an image relating to a wrinkle care on a user representative image based on the determined wrinkle care user presentation information; and
displaying the created information display image.

19. The computer-implemented method for supporting wrinkle care according to claim 10, wherein the wrinkle care user presentation information differs depending on the detected wrinkle disappearing time.

20. The wrinkle care support device according to claim 1, wherein the wrinkle care user presentation information differs depending on the detected wrinkle disappearing time.

* * * * *